United States Patent [19]

Nowak

[11] Patent Number: 5,358,873
[45] Date of Patent: Oct. 25, 1994

[54] METHOD FOR DETERMINING ADULTERATION OF GASOLINES

[75] Inventor: Anthony V. Nowak, Fullerton, Calif.

[73] Assignee: Atlantic Richfield Company, Los Angeles, Calif.

[21] Appl. No.: 139,365

[22] Filed: Oct. 20, 1993

Related U.S. Application Data

[63] Continuation-in-part of Ser. No. 135,864, Oct. 13, 1993, abandoned, which is a continuation of Ser. No. 920,071, Jul. 27, 1992, abandoned.

[51] Int. Cl.$^5$ .............................................. G01N 35/08
[52] U.S. Cl. ...................................... 436/56; 436/690; 436/178
[58] Field of Search ................... 436/56, 60, 178, 165, 436/139; 44/59; 252/408.1

[56] References Cited

U.S. PATENT DOCUMENTS

| | | | |
|---|---|---|---|
| 3,976,572 | 9/1976 | Reilk | 210/94 |
| 4,049,393 | 9/1977 | Orelup | 44/59 |
| 4,514,503 | 4/1985 | Orelup | 436/60 |
| 4,717,671 | 1/1988 | Melpodor | 436/39 |
| 4,918,020 | 4/1990 | Nowak | 436/56 |
| 5,229,298 | 7/1993 | Zoulmalan | 436/111 |
| 5,244,808 | 9/1993 | Nowak | 436/50 |

*Primary Examiner*—N. Bhat
*Attorney, Agent, or Firm*—Michael E. Martin

[57] ABSTRACT

Reformulated and other automotive motor gasolines may be analyzed to detect adulteration with gasolines containing a Rhodamine B base marker dye by mixing a small sample of the suspected fuel in a vial containing a small quantity of unbonded flash chromatography-grade silica. The presence of such marker dye in the suspect sample will color the silica red. The coloration may be detected in fuel samples which also contain red or blue grade identification dyes, detergent additives and oxygenates such as ethanol and MTBE.

14 Claims, No Drawings

METHOD FOR DETERMINING ADULTERATION OF GASOLINES

CROSS REFERENCE TO RELATED APPLICATION

This application is a continuation-in-part of U.S. patent application Ser. No. 08/135,864, filed Oct. 13, 1993, now abandoned, which is a continuation of Ser. No. 07/920,071, filed Jul. 27, 1992, now abandoned.

BACKGROUND OF THE INVENTION

1. Field of the Invention

The present invention pertains to a method for determining adulteration of motor gasolines and similar hydrocarbon fuels by determining the presence of a marker dye in a small sample of the fuel with chromatography-grade silica which selectively extracts the dye from the fuel and is imparted with a color which is easily visually detected.

2. Background

The complexities involved in the production and distribution of automotive motor gasolines and similar fuels has given rise to the wide use of certain types of marker or identification additives or "dyes" in the fuels. For example, it is common to use both visible and non-visible identification dyes to distinguish one grade or octane rating of automotive gasoline from another grade. It has also become increasingly necessary, and may be legislatively mandated, that reformulated gasolines, i.e., those which are less likely to emit unwanted hydrocarbon vapors into the atmosphere or result in undesired combustion products, be identifiable from non-reformulated fuels. Moreover, the use of certain additives in automotive gasolines such as oxygenates, octane-enhancing additives and detergent additives increases the difficulty in testing the fuels to determine the presence of other additives such as brand or grade identification additives.

A process for testing of gasolines to determine the presence or concentration of an identifying additive associated with brand, grade or specific fuel composition should meet certain criteria. The test must be simple to perform in the field and require little, if any, sophisticated equipment. The test should require the use of as small a sample of the fuel as possible in order to minimize the hazards associated with handling the fuel and problems associated with disposal of the test sample. These desiderata are constantly being sought in the development of improved methods of testing automotive gasolines. However, the complex chemistry of automotive gasolines and the various additives and identification materials that are used in these fuels makes the achievement of the above-mentioned objectives particularly difficult.

By way of example, my U.S. Pat. No. 4,918,020, issued Apr. 17, 1990 and assigned to the assignee of the present invention, discloses and claims a method for analyzing marker dyes in automotive gasolines using solid-phase extraction onto a packed column followed by the formation of a colored complex in the column by reacting the separated marker dye with a color-forming reagent and then determining the color intensity of the colored complex to indicate the concentration of the marker dye in the fuel sample. Although this method is advantageous in certain respects, it does require the use of a separation column and test liquids which must be carried by the person performing the test in the field. Moreover, the particular method described in the '020 patent may not work with fuels which have been injected with certain additives such as oxygenates.

Another method of analyzing marker dye concentrations in petroleum fuels is described in U.S. patent application Ser. No. 07/825,343, filed Jan. 24, 1992 by Sarkiss Zoumalan and also assigned to the assignee of the present invention. The method described in the Zoumalan application overcomes some of the problems associated with testing gasolines to which oxygenates have been added but also requires the use of certain test liquids and sophisticated composition analysis equipment. Accordingly, the complexities found in both of the above-mentioned test methods are not advantageous when it is desired to test gasolines for adulteration in the field, that is at bulk storage terminals or at the storage tanks for retail dispensing stations. It is to this end that the discovery and method of the present invention overcomes some of the problems associated with testing automotive motor gasolines for improper mixing or adulteration, particularly at various distribution and dispensing facilities.

SUMMARY OF THE INVENTION

The present invention provides a unique method for determining the presence of a marker additive in automotive motor gasolines and similar hydrocarbon fuels.

In accordance with one important aspect of the present invention, it has been discovered that a particular type of petroleum fuel marker additive comprising a Rhodamine dye, more particularly Rhodamine B base, may be easily detected by mixing a small sample of fuel which has been marked with the additive with a selective solid phase extractant. In particular, a desirable solid phase extractant for use with the method of this invention is unbonded flash chromatography-grade silica.

More particularly, the method of the present invention contemplates the mixing of a small sample of fuel to extract the marker additive with unbonded flash chromatography-grade silica of about 40 micron particle size. Still further, a small amount of a fuel such as a reformulated automotive motor gasoline (sample size, 2 to 5 milliliters) marked with the above-mentioned additive dye may be added to a small amount (about 25 mg) of the extractant silica in a vial and swirled to thoroughly mix the sample with the extractant. It has been discovered that the extractant selectively extracts the marker additive from the gasoline and is imparted with a red color which is easily visually detected.

The present invention is particularly useful to determine the presence of the above-mentioned marker additive, in small concentrations as low as 1 ppm, even though the gasolines may also include grade identification dyes and other performance additives such as oxygenates and detergent additives.

Significant advantages of the method of the present invention include the lack of requirement to transport liquid reagents and complex equipment into the field. It is only necessary to carry one or more small vials containing a small amount of the silica extractant, which may be prepackaged before going into the field to perform the adulteration tests. Accordingly, prepackaging the extractant material eliminates the requirement of handling fine-powdered silica, for example, at the test site. The extractant vials may be kept available indefinitely, without any special care, as long as they are sealed sufficiently to prevent moisture adsorption.

Since the method of the present invention requires only a small amount of fuel sample, it inherently minimizes the hazards associated with handling larger volumes of volatile fuels and test reagents required with other test methods. Still further, since the fuel sample is not contaminated with any chemicals, it may be easily returned to its storage container by merely filtering the sample to remove the extractant particles, thereby eliminating even minimal fuel disposal requirements. Yet a further advantage of the method of the present invention is that the large surface area provided by the extractant material assures that the extraction of the marker additive from the fuel is substantially complete, thereby increasing the sensitivity of the test method.

Those skilled in the art will further appreciate the above-mentioned advantages and superior features of the present invention, together with other important aspects thereof, upon reading the detailed description which follows.

DESCRIPTION OF PREFERRED EMBODIMENTS

The anticipated large utilization of environmentally beneficial reformulated gasolines will require major and expensive modifications to petroleum refineries in order to produce such gasolines. Accordingly, such gasolines will likely be more expensive to purchase than the current non-reformulated gasolines. The anticipated adulteration of reformulated gasolines at various points in the distribution network has brought into consideration the requirement that a so called marker or tracer additive be added to all non-reformulated gasolines so that the adulteration of reformulated gasolines can be detected. As mentioned above, any field test method for determining the presence of additives in petroleum fuels, such as automotive gasolines, should be uncomplicated so that relatively untrained personnel can easily perform an accurate test. Still further, it is desirable that such types of tests be very sensitive so that only small quantities of the marker additive need be used to mark the gasolines, as required, and that only a small sample of the fuel be used for test purposes. As also mentioned previously, it is important and desirable to eliminate the need for any delicate and expensive analytical equipment or hazardous test liquids as part of the test procedure.

Reformulated gasolines will, in many instances, also include detergent and combustion-enhancing additives which will likely be injected into the fuel after production at some point in the distribution system. Since the method of the present invention contemplates carrying out tests near the terminal point in the distribution system, that is at the retail-dispensing station storage tank or at the wholesale distribution facility storage tank, it is necessary that the test method be capable of detecting the presence of the marker additive in the presence of substantially all of the other additives that will be present in the fuel before it is put to its final use. One marker additive which is considered particularly suitable for the method of the present invention includes a Rhodamine dye composition in the amount of 20% to 30% of the total additive composition mixed with 2-Pyrrolidinone, 1-Methyl—in the range of 40% to 70% of the total additive composition. In particular, the Rhodamine dye is Rhodamine B base. The subject marker is non-visual when injected into automotive gasolines at the recommended dosage rate. In accordance with the present invention, however, it has been determined that this marker dye or additive is easily visually detected without the addition of a color-forming reagent when using the method of the present invention. Moreover, it is contemplated that the method of the invention may be used to detect Rhodamine B, Rhodamine G, Rhodamine 3B, Rhodamine 6G, Rhodamine S and Sulforhodamine B.

The method of the present invention differs from what has been done in the prior art in regard to liquid/liquid extraction methods or solid-phase extraction methods. Although the field test method in accordance with the present invention is basically a solid-phase extraction of the marker additive from the gasoline with visual detection, it is not necessary to pass the fuel sample through a solid-phase extraction column such as is contemplated by the method of U.S. Pat. No. 4,918,020 or my U.S. Pat. No. 5,244,808, issued Sep. 14, 1993. A small amount of a gasoline sample, in the range of 2.0 to 5.0 ml. may be added to a small amount (25.0 mg.) of a particular solid extractant in a small vial and swirled. The extractant contemplated by the method of the invention is unbonded flash chromatography-grade silica, preferably of about 40 micron particle size. Such material is available from J. T. Baker, Inc., Phillipsburg, N.J., although other brands of silica normally used as chromatographic packing material may also be used in the method of the present invention. The small quantity of extractant may be placed in disposable scintillation vials, 20 ml. size, such as those available from Kimble Glass, inc., Vineland, N.J. In accordance with the present invention, the sample of gasoline in the above-mentioned volume range is merely poured into the vial containing the extractant, and the vial is swirled for about ten (10) seconds at ambient atmospheric conditions of temperature and pressure normally fit for human habitation. It has been observed that the silica extractant material selectively extracts Rhodamine B base, as well as similar polar additives from the gasoline, and a red color is imparted to the extractant material which is easily visually detected. Specific examples of the method of the present invention are further described herein.

EXAMPLE I

A sample of premium reformulated gasoline, ARCO EC-P brand, available from ARCO Petroleum Products Company, Los Angeles, Calif., was provided, This gasoline is marked with a red, grade-identification dye, for example, DuPont Oil Red B Liquid. A sample of the red dyed premium reformulated gasoline (ARCO EC-P) was adulterated with 10% w/v non-reformulated gasoline containing 1 ppm w/v of a Rhodamine marker dye composition comprising 20%–30% Rhodamine B base and 40%–70% 2-Pyrrolidinone, 1-Methyl. This resulted in a marker dye concentration of 0.1 ppm w/v in the mixture. The sample was mixed in the 20 ml. vial at conventional laboratory ambient temperature and pressure conditions with 25 mg. of the unbonded flash chromatography-grade silica, 40 micron particle size. The sample was swirled in the vial for ten (10) seconds. The red coloring of the silica, indicating the presence of the marker dye, was easily discerned even though the bulk gasoline sample was tinted red from the grade-identification dye.

The above-mentioned test was repeated with a fresh sample of the silica extractant in a clean vial and testing neat ARCO EC-P reformulated gasoline. The silica remained uncolored. The present invention contemplates that, for comparison purposes, an unadulterated gasoline sample may be tested in the field and compared with the suspected sample to verify the difference in coloration of the silica.

EXAMPLE II

The above-mentioned test was repeated at the same conditions with a previously unused vial of the silica extractant, using a sample of ARCO EC-1 gasoline, available from ARCO Petroleum Products Company. This gasoline is marked with a blue marker dye to distinguish its grade from the higher grade of ARCO EC-P automotive motor gasoline. A sample of the ARCO EC-1 was adulterated with 10% v/v non-reformulated gasoline containing 1 ppm w/v of the marker dye composition used in Example I. The red coloration visible on the silica was even easier to detect in the blue-dyed gasoline than with the red-dyed gasoline, and a distinct red coloring of the silica was observed. The ability of the extractant to selectively remove the above-mentioned type of marker dye and not the grade-identification dyes is a major advantage of the present invention.

The unbonded silica used in the described method is decidedly acidic in nature. The basic Rhodamine B base binds with acidic hydroxyl groups on the silica and is firmly held on its surface. This accounts for the selective and highly sensitive ability of the described method to detect the red marker dye even in the presence of a red grade differentiation dye. All of the marker dye is thereby removed from solution in this manner.

Essentially all branded motor gasolines distributed by the major U.S. petroleum marketers contain detergent additives whose function is to clean the fuel injectors of internal combustion engines. Detergent additives are usually present in the gasolines at 0.5% to 1.0% by volume, depending on the gasoline grade. These detergent additives are injected into the gasoline at the bulk storage and dispensing terminal facilities, usually as the gasoline is being loaded into delivery tank trucks. Detergent additive compositions are typically polymeric materials containing nitrogen as an amine functionality on the polymer chain. These additives share some chemical similarities to gasoline marker dyes and are often extracted from gasolines when using solid-phase extraction techniques along with the marker dye whose identity is being sought. Since the detergent additives are present in relatively large concentrations compared to the marker additives, they often interfere with the selective elution of the marker additive as well as with subsequent spectrometric absorption measurements.

Accordingly, the experiments described above in Examples I and II were repeated with gasolines to which the polymeric detergent additive compositions were added in the normal range found in gasolines ready for delivery to the retail purchaser. Samples of ARCO EC-1, ARCO EC-P and ARCO Clear, the latter a non-reformulated gasoline which is not dyed, were adulterated with 10% v/v non-reformulated gasoline containing 1.0 ppm w/v of the above-described Rhodamine marker dye. Each sample contained 0.10 ppm marker dye in the final mixture. Each of the above-mentioned samples was subjected to the detection method of the present invention, and no adverse effect of the detergent additive was observed. Test conditions were similar to those described above in Examples I and II. Distinct red coloration of the silica extractant material was easily observed with each of the gasolines, as was the case in Examples I and II with gasoline samples which did not contain any detergent additives.

Finally, tests were carried out with samples of gasoline containing oxygenate materials, such as MTBE (methyl tertiary butyl ether), a commonly used oxygenate additive. Other oxygenates, such as ethanol, are also used in reformulated automotive gasolines.

In order to determine the effect on the method of the present invention of the presence of oxygenates, a pseudo-reformulated fuel was made up using samples of ARCO Clear automotive gasoline, with fuel-grade ethanol at 10% v/v concentration, and then adulterated with 10% v/v non-reformulated fuel containing 1.0 ppm of the Rhodamine marker dye composition. A 3.0 ml. sample of this gasoline was subjected to the method of the invention and did not affect the coloration of the extractant silica. In the above-mentioned test, the silica extractant clearly exhibited the red coloration, showing the presence of the marker additive. Accordingly, the present invention may be used with ethanol-containing gasolines as well as gasolines containing the MTBE oxygenate.

A preferred experimental procedure in accordance with the present invention includes adding 25 mg. of the above-mentioned silica composition to a 20 ml. disposable scintillation vial, followed by adding 2.0 to 5.0 ml. of the gasoline sample to the vial. The vial is capped and swirled gently, followed by cessation of motion to allow the silica particles to settle to the bottom of the vial. At this point, observation of the color of the silica is made. It should assume a red, almost fluorescent, color if the above-mentioned type of marker additive is present. The intensity of the color will depend on the concentration of the marker in the gasoline and the degree of adulteration. As mentioned previously, a similar gasoline sample known to contain no marker additive may be tested and compared with the suspected sample for comparison purposes, particularly when attempting to discern very low adulteration levels.

Although preferred embodiments of the present invention have been described hereinabove, those skilled in the art will recognize that various substitutions and modifications may be made to the inventive method without departing from the scope and spirit thereof, as recited in the appended claims.

What is claimed is:

1. A method for determining the presence of a marker dye composition in automotive motor gasoline, said marker dye composition including a Rhodamine dye, said method comprising the steps of:

mixing a sample of gasoline suspected of containing said marker dye with a quantity of fine-ground silica in a container and determining a change in the color of the silica to detect the presence of said Rhodamine dye.

2. The method set forth in claim 1 wherein:

said silica comprises unbonded flash chromatography-grade silica.

3. The method set forth in claim 1 or 2 wherein:

said silica has a particle size of about 40 microns, maximum diameter.

4. The method set forth in claim 1, including the step of:

mixing a sample of gasoline without said Rhodamine dye with a sample of said silica and comparing the coloration of silica with the sample containing no Rhodamine dye with the sample suspected of containing said Rhodamine dye.

5. The method set forth in claim 1 wherein:
the gasoline sample includes a red identification dye.

6. The method set forth in claim 1 wherein:
the gasoline sample includes a blue identification dye.

7. The method set forth in claim 1 wherein:
the gasoline sample includes a detergent additive therein.

8. The method set forth in claim 1 wherein:
the gasoline sample includes an oxygenate additive therein.

9. The method set forth in claim 8 wherein:
the gasoline sample contains MTBE as an oxygenate additive.

10. The method set forth in claim 8 wherein:
the gasoline sample includes ethanol as an oxygenate additive.

11. A method for determining the presence of a marker dye composition in automotive motor gasoline, said marker dye composition comprising 20%–30% Rhodamine B base and 40%–70% 2-Pyrollidinone, 1-Methyl, said method comprising the steps of:
mixing a sample of gasoline suspected of containing said marker dye with fine-ground, unbonded, flash chromatography grade silica in a container and determining a change in color of the silica to detect the presence of said Rhodamine B base in said marker dye.

12. The method set forth in claim 11, including the step of:
mixing a sample of gasoline without said marker dye with a sample of said silica and comparing the coloration of silica with the sample containing none of said marker dye with the sample suspected of containing said marker dye.

13. A method for determining the presence of a marker dye in automotive motor gasoline, said marker dye comprising Rhodamine B base, said method comprising the steps of:
providing a sample of motor gasoline known to contain a detergent additive, an oxygenate additive and a grade identification dye therein;
mixing said sample of gasoline with fine-ground silica having a particle size of about 40 microns maximum diameter in a container and determining a change in color of the silica to detect the presence of said Rhodamine B base.

14. The method set forth in claim 13, including the step of:
mixing a sample of gasoline without said marker dye with a sample of said silica and comparing the coloration of said silica with the sample containing no Rhodamine B base with the sample suspected of containing said Rhodamine B base.

* * * * *